(12) United States Patent
Kimura et al.

(10) Patent No.: US 10,417,754 B2
(45) Date of Patent: Sep. 17, 2019

(54) INSPECTION SYSTEM

(71) Applicant: OMRON Corporation, Kyoto-shi, Kyoto (JP)

(72) Inventors: Yuki Kimura, Kyoto (JP); Akira Matsui, Joyo (JP); Shingo Inazumi, Amagasaki (JP)

(73) Assignee: OMRON Corporation, Kyoto (JP)

( * ) Notice: Subject to any disclaimer, the term of this patent is extended or adjusted under 35 U.S.C. 154(b) by 118 days.

(21) Appl. No.: 15/448,487

(22) Filed: Mar. 2, 2017

(65) Prior Publication Data
US 2018/0005365 A1 Jan. 4, 2018

(30) Foreign Application Priority Data

Jun. 30, 2016 (JP) ................. 2016-130458

(51) Int. Cl.
| | |
|---|---|
| *H04N 7/18* | (2006.01) |
| *G06T 7/00* | (2017.01) |
| *B25J 9/00* | (2006.01) |
| *G01N 21/88* | (2006.01) |
| *G01B 11/10* | (2006.01) |
| *G01B 11/24* | (2006.01) |
| *G01N 21/95* | (2006.01) |
| *G01N 21/952* | (2006.01) |

(Continued)

(52) U.S. Cl.
CPC ............ *G06T 7/0004* (2013.01); *B25J 9/0087* (2013.01); *G01B 11/105* (2013.01); *G01B 11/14* (2013.01); *G01B 11/245* (2013.01); *G01B 11/2416* (2013.01); *G01N 21/8806* (2013.01); *G01N 21/8851* (2013.01); *G01N 21/952* (2013.01); *G01N 21/9515* (2013.01); *H04N 7/181* (2013.01); *G01N 2021/8887* (2013.01)

(58) Field of Classification Search
CPC ...... B25J 9/0087; G01B 11/105; G01B 11/14; G06T 7/0004
USPC ........ 348/92, 94, 95, 135, 180, 125; 73/600, 73/598
See application file for complete search history.

(56) References Cited

U.S. PATENT DOCUMENTS

| | | | | |
|---|---|---|---|---|
| 5,077,477 A | * | 12/1991 | Stroman | ............... B07C 5/3416 209/577 |
| 2013/0202195 A1 | | 8/2013 | Perez Cortes et al. | |
| 2015/0254828 A1 | | 9/2015 | Beach et al. | |

FOREIGN PATENT DOCUMENTS

| | | |
|---|---|---|
| JP | 2009-014696 | 1/2009 |
| WO | WO 2005/022076 | 3/2005 |
| WO | WO 2011/072157 | 6/2011 |

OTHER PUBLICATIONS

Extended European Search Report for European Application No. EP 17 15 9082 dated Sep. 29, 2017 in 9 pages.

* cited by examiner

*Primary Examiner* — Jefferey F Harold
*Assistant Examiner* — Jean W Desir
(74) *Attorney, Agent, or Firm* — Knobbe, Martens, Olson & Bear, LLP (57) ABSTRACT

An inspection system is provided with an inspection device configured to examine the external features of an object; and a control device for controlling the inspection device; the inspection device including: a substantially column-shaped first barrel that includes a first through hole configured for an object to pass therethrough; and a plurality of imaging units provided on the inner peripheral surface which forms the first through hole in the first barrel; and the control device including: an image pro- (Continued)

cessing unit configured to process an image captured and output by each of the imaging units for the purpose of inspection.

16 Claims, 9 Drawing Sheets

(51) Int. Cl.
  *G01B 11/14* (2006.01)
  *G01B 11/245* (2006.01)

INSPECTION SYSTEM

FIELD

The present invention relates generally to an inspection system, and more specifically to an inspection system that captures an image of an object being inspected.

BACKGROUND

In Factory Automation (FA) and related fields, an inspector selects a sample of products and examines the entire outside for bumps and pits or scratches when performing a visual inspection of, for example, components during manufacture, of half-finished products, or of products prior to delivery. However, performing this kind of inspection for all products would be time consuming and labor intensive.

The use of machines which combine image sensors, measurement sensors, and robots for inspections has been proposed as a way to counter this problem. For instance, Japanese Patent Publication No. 2009-14696 (Patent Document 1) discloses a visual inspection device that employs a robot. Here, Japanese Patent Publication No. 2009-14696 describes providing the robot with a camera and an illumination unit so that the visual inspection device may acquire the image information needed to perform a visual inspection of the inspection object. A robot controller directs the robot to move the camera relative to the inspection object, and operates the illumination unit together with moving the camera.

Technical Problem

While the technology proposed in Japanese Patent Publication No. 2009-14696 reduces the amount of labor, moving the robots in order to move the camera and the illumination unit in order to perform a visual inspection of the entire outside of the product takes time; moving the robots also significantly lengthens the inspection process which creates problems where the amount of time needed for an inspection becomes greater than the amount of time that can be available.

Therefore, embodiments of the invention aim to provide an inspection system capable of reducing the amount of time taken for inspection.

SUMMARY

An inspection system according to embodiments of the invention is provided with an inspection device configured to examine the external features of an object, and a control device for controlling the inspection device. The inspection device is provided with a first barrel that is substantially column-shaped with a first through hole configured for an object to pass therethrough, and a plurality of imaging units provided on the inner peripheral surface which forms the first through hole in the first barrel. The control device includes an image processing unit that processes an image captured by and output from each of the imaging units for the purpose of inspection.

Hereby, an image of substantially all the external features of the object and a visual inspection result may be obtained by merely passing the object through a first through hole.

The control device may further include a communication unit configured for communication with an external device. The external device may include: a support device including a first support configured to support an object; and a drive unit. The control device may cause the communication unit to transmit a control signal to the support device, said control signal configured to control the drive unit to cause the first support to pass through the first through hole while supporting the object.

Hereby, the first support supports the object as the object passes through the through hole.

The support device may further include a second support configured to support the object; and the control device may cause the communication unit to transmit a control signal to the support device, said control signal configured to control the drive unit to cause the second support to receive the object from the first support after the first support passes through the first through hole.

Hereby, the second support may receive the object after the object passes through the through hole supported by the first support.

The inspection device may further include a light source configured to illuminate inside the first through hole. Hereby, illumination light may be provided when capturing the image.

The inspection device may include: a substantially circular second barrel that includes a second through hole configured for an object to pass therethrough; and a plurality of measurement sensors provided on the inner peripheral surface of the second barrel and configured to measure the external features of the object. The control device may include: a measurement processing unit configured to process the measurement values output from the measurement sensors for the purpose of inspection.

Hereby, a measurement value, such as the size of substantially all the external features of the object may be obtained by merely passing the object through a second through hole.

The first barrel and the second barrel may be stacked along a virtual axis passing through the first through hole and the second through hole, with said virtual axis corresponding to a route along which the object passes.

Hereby, a visual inspection of and a measurement such as the size of substantially all the external features of the object may be obtained by merely passing the object along a virtual axis.

An inspection system according to another embodiment of the invention includes an inspection device configured to examine the external features of an object; and a control device for controlling the inspection device. The inspection device may include: a substantially column-shaped second barrel that includes a second through hole configured for an object to pass therethrough; and a plurality of measurement sensors provided on the inner peripheral surface of the second barrel and configured to measure the external features of the object. The control device may include: a measurement processing unit configured to process the measurement values output from the measurement sensors for the purpose of inspection.

Hereby, a measurement value, such as the size of substantially all the external features of the object may be obtained by merely passing the object through a second through hole.

Effects

In embodiments of the present invention visual inspection results and a measurement value such as size may be simultaneously acquired for almost all the external features of the object when the object passes through a through hole.

DETAILED DESCRIPTION

Embodiments of the present invention are described in detail with reference to the drawings. The same or corresponding elements within the drawings are given the same reference numerals and the explanations therefor are not repeated.

In the embodiments an object for inspection is referred to as a work piece. Although a work piece is exemplified as a part of a machine in the embodiment a work piece is not so limited.

Overview

An inspection system is provided with an inspection device for examining the external features of a work piece, and a control device for controlling the inspection device. The inspection device is provided with a first barrel that is substantially column-shaped with a first through hole through which a work piece can pass, and a plurality of imaging units provided on the inner peripheral surface which forms the first through hole in the first barrel. The control device includes an image processing unit that processes an image captured by and output from each of the imaging units for the purpose of inspection.

Accordingly, the plurality of imaging units provided on the inner peripheral surface are capable of obtaining images of substantially all the external features of the work piece by merely passing the work piece through the through hole; thus, it is possible to reduce the amount of time required for inspecting the work piece. As a result, it is possible to inspect all the products within a desired time without depending on inspecting a sample of work pieces.

First Embodiment

Figure 1:
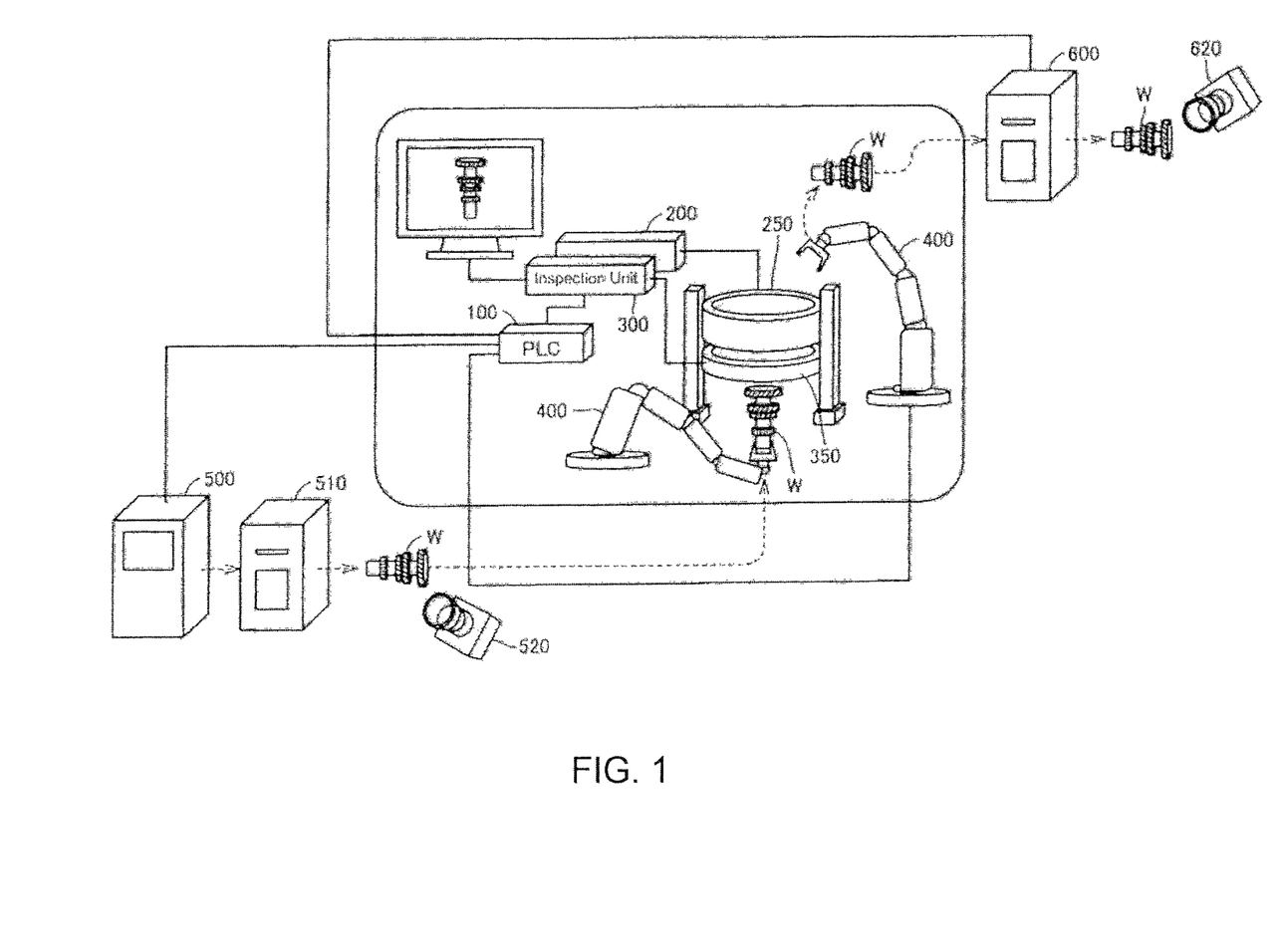
FIG. 1 is a configuration diagram illustrating an overview of an inspection system according to a first embodiment.

FIG. 1 is a configuration diagram illustrating an overview of an inspection system according to a first embodiment. The inspection system is included on a production line and carries out inspection as a robot 400 (later described) grabs (supports) an individual object to be inspected (work piece W) from work pieces bulk loaded onto a tray or the like.

The inspection system is a programmable logic controller 100 (PLC 100) with inspection units 200 and 300, and a robot 400 connected thereto (FIG. 1). A measurement device 350 is connected to the inspection unit 300, and an imaging device 250 is connected to the inspection unit 200. The control device in the inspection system according to this embodiment is collectively composed of the inspection units 200 and 300, and the PLC 100.

The PLC 100 is provided with a machining device 500 for processing the work piece, a laser marker 510 for applying an identification mark (ID) to the surface of the processed work piece, and a code reader 520 for reading the ID mark applied to the marked work piece. The ID mark may include a barcode.

The inspection system may further include a post production device 600 into which the inspection results output from the PLC 100 enter, and based on said inspection results the post production device 600 determines a grade for the work piece W. The IDs of the work pieces W graded by the post production device 600 are read by a code reader 620. Hereby, a work piece W can be categorized based on the grade to control quality. The PLC 100 may also determine the parameters for controlling the machining device 500 on the basis of the inspection results, and output the parameters determined to the machining device 500. The machining device may thereby be controlled to operate according to the aforementioned parameters to allow the precision of machining the work piece W to change in accordance with the inspection results. Note that each of the components in FIG. 1 may communicate with each other via wired or wireless communication.

The Imaging Device and the Measurement Device

Figure 2:
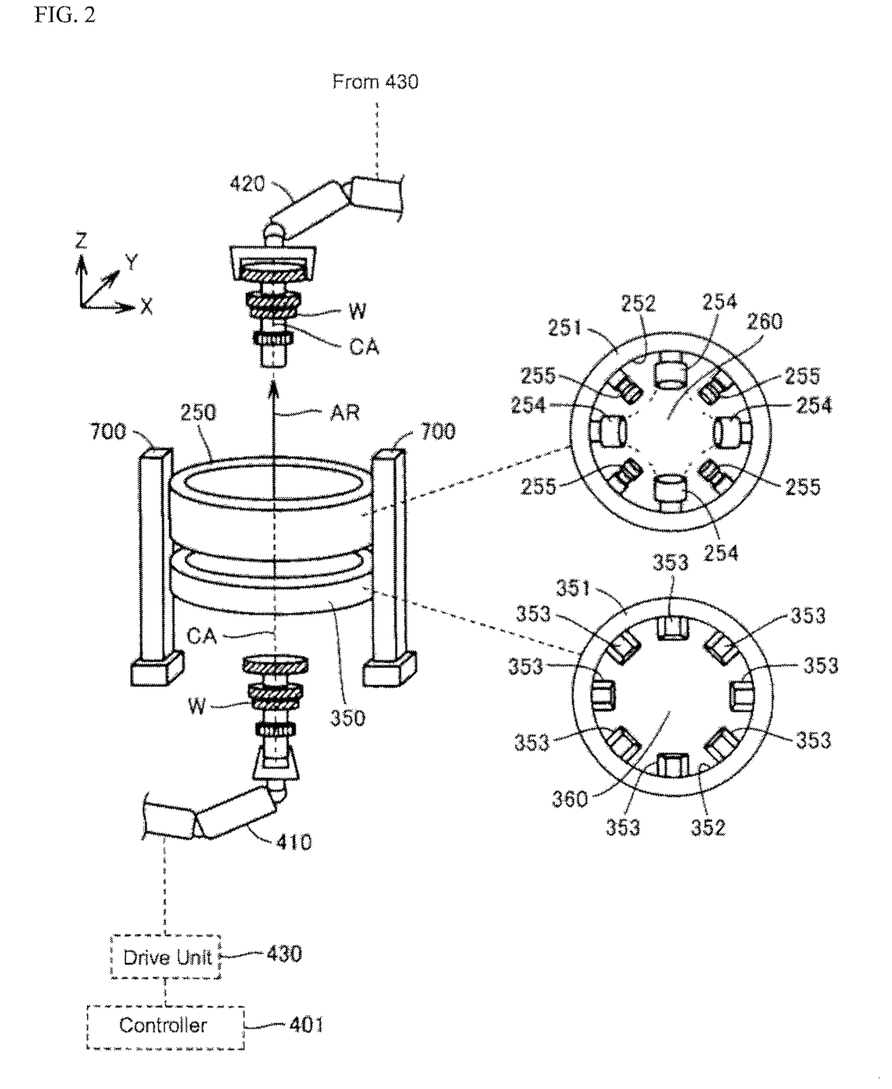
FIG. 2 is a schematic view of a configuration of the imaging device 250 and the measurement device 350 depicted in FIG. 1.

FIG. 2 is a schematic view of a configuration of the imaging device 250 and the measurement device 350 depicted in FIG. 1. The imaging device 250 is provided with a substantially column-shaped first barrel 251 that includes a first through hole 260 through which a work piece W can pass. The imaging device 250 is further provided with a plurality of imaging units 255 and a plurality of illumination devices 254 which act as light sources; the imaging units 255 and the illumination devices 254 are arranged along the inner peripheral surface 252 which forms the first through hole 260 of the first barrel 251. The imaging angle (angle) of an imaging unit 255 is variable. As is later described, this embodiment adjusts each of the imaging units 255 and each of the illumination devices 254 so that the imaging directions and illumination directions are toward the center of the first through hole 260. The illumination devices 254 radiate light at an angle that creates no halation at the surface of the object (i.e., the surface of the work piece W). Hereby, the image captured contains no halation and is of uniform intensity.

The imaging device 250 primarily includes optics composed of lens and the like, and an imaging element such as a charge coupled device (CCD) or a complementary metal oxide semiconductor (CMOS). An illumination device 254 mainly includes a light source such as a light emitting diode (LED) or a halogen lamp.

The measurement device 350 is provided with a substantially column-shaped second barrel 351 that includes a second through hole 360 through which a work piece W can pass. The measurement device 350 is further provided with a plurality of measurement sensors 353 along the inner peripheral surface 352 which forms the second through hole 360 of the second barrel 351. To perform contactless measurement, a measurement sensor 353 uses light from a laser or an LED, or electromagnetic waves such as ultrasonic waves to measure the topology of the work piece W. For instance, the measurement device 350 performs three-dimensional (3-D) measurement.

As is later described, this embodiment adjusts the electromagnetic wave measurement axis of each of the measurement sensors 353 to coincide with the direction toward the center of the second through hole 360.

While the first barrel 251 and the second barrel 351, and the first through hole 260 and the second through hole 360 are described as substantially (circular) columns, these components may be perfectly circular or elliptical. The first through hole 260 and the second through hole 360 are almost the same size and shape. The first and second barrels 251, 351 and the first and second through holes 260, 360 are not limited to being substantially circular and may be polygons.

Robot 400

A robot 400 is depicted in relation to the imaging device 250 and the measurement device 350 (FIG. 2). The robot 400 includes a hand mechanism for grabbing a work piece W, and a joint mechanism for positioning the hand mechanism in a data desired location and direction. Movement of the robot 400 is controlled by a robot controller 401.

The robot 400 is provided with a first support 410 and a second support 420 which are essentially manipulator arms, and a drive unit 430 moving van mechanism and the joint mechanism via the manipulator arms. The drive unit 430 is essentially a servo motor. The drive unit contains a motor connected to the rotation shafts of the hand and joint mechanisms, an encoder, and a driver. The drive unit 430 detects the rotational angle and rotation speed of the motor shaft with the encoder and feeds the detection result back to the motor driver. The motor driver takes the feedback of the detection value and a control value entering from the robot controller 401 and generates a control signal such that the difference in the values is zero; the motor driver then outputs that control signal to the motor. Hereby the motor rotates according to the control signal, whereby for example, the hand mechanism and the joint mechanism rotate, and the joint of the arm of the first support 410 and the second support 420 move together with the rotation of the motor.

Movement of the Robot Arm

The object to be examine, i.e., the work piece W may be placed on a tray (not shown). The robot controller 401 identifies the location and positioning of a work piece W on the basis of information representing the center position (central axis CA, FIG. 2) of the work piece W; this information is obtained from an image of the work piece W on the tray and calculated computed by the PLC 100. The robot controller also generates a command for output to the drive unit 430 that positions the hand mechanism of the first support 410 on the robot 400 so that the hand mechanism is positioned at a location in a direction capable of grasping the work piece W; this command is generated on the basis of the aforementioned identified location and positioning of the work pieces W. The first support 410 initiates an operation, via the drive unit 430, to grab the work piece W in response to the command. Hereby, the work piece W is held in a predetermined position such that a direction extending along the central axis CA thereof coincides with the direction extending along a virtual axis AR.

Referring to FIG. 2 the plurality of barrels (i.e., the first barrel 251, and the second barrel 351 are layered along the axis AR. The route along which the work piece W passes (i.e., moves through the first through hole 260 and the second to whole 360 coincides with the axis AR. For instance, the axis AR passes through the center (center of gravity) of a substantially circular shape defined by the inner peripheral surface 252 of the first through hole 260 and the center (center of gravity) of the substantially circular shape defined by the inner peripheral surface 352 of the second through hole 360.

The PLC 100 transmits a control signal to the robot controller 401 for controlling the drive unit 430. The control signal represents a signal that controls the drive unit 430 so that the first support 410 moves along the axis AR extending along busy access in FIG. 2, and passes through the second through hole 660 and the first through hole 260 while the robot holds the work piece W at the predetermined position. The PLC 100 also transmits a control signal to the robot controller 401 for controlling the drive unit 430 so that the second support 420 receives the work piece W that has passed through the first through hole 260 from the first support 410 with the work piece W in the aforementioned predetermined position.

The above-mentioned predetermined position is equivalent to the state that the first support 410 grabs a part (one end) of the work piece W as shown in the figure. Accordingly, the plurality of measurement sensors 353 positioned roughly about the entire periphery of the work piece W measure the topography of the work piece W when the same moves through the second through hole 360; further, the plurality of imaging units 255 positioned about the entire periphery of the workpiece W capture the work piece W as the same moves through the first through hole 260 and is illuminated from directions about the entire periphery thereof.

The predetermined position determined on the basis of the central axis CA of the work piece W allows the imaging device 250 to capture an image of the work piece W from all directions, and allows the measurement device 350 to measure the surface topography from all directions about the work piece W. This positioning may be determined in advance by experimentation. Note that the predetermined position of the work piece W is preferably determined from the shape and size thereof, and is not limited to the positioning illustrated in FIG. 2.

Measuring and Capturing Sites on the Work Piece

Figure 3:
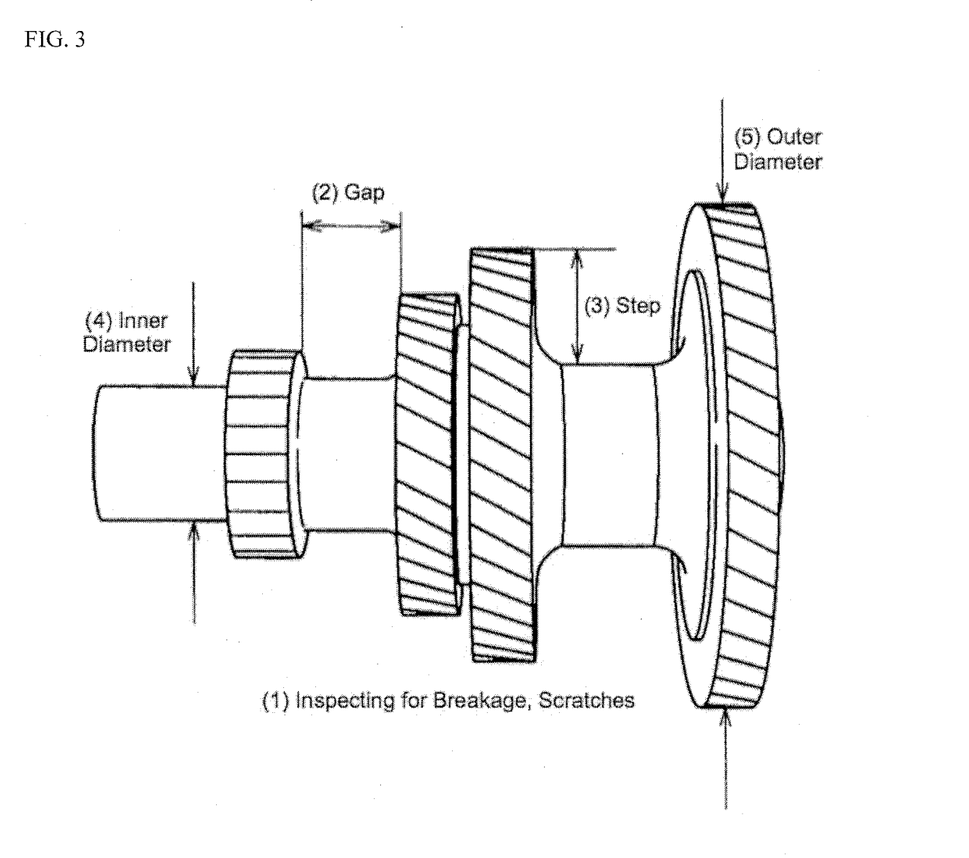
FIG. 3 illustrates one example of a work piece W in the first embodiment.

FIG. 3 illustrates one example of a work piece W in the first embodiment. Referring to FIG. 3, the measurement device 350 measures the inner diameter (4), and the outer diameter (5), the step (3) and the gap (2) on the work piece W. The imaging device 250 captures an image of a site (1) inspected to determine whether or not there are scratches or damage on the surface of the work piece W.

As illustrated in FIG. 2 on FIG. 3, the site gripped by the first support 410 so that the work piece W is in the above-mentioned predetermined position is preferably a site that is not to be measured or captured, i.e. none of the sites (1) to (5).

The PLC 100

The PLC 100 is, for example, a computer having a general-purpose architecture; executing programs (command codes) previously installed there on allows the PLC 100 to provide the functions of the embodiment. These kinds of programs may be run while stored on various kinds of recording media, or may be installed on the PLC 100 via a network.

When implementing the embodiment through such a general-purpose computer, an operating system (OS) may be installed on the general-purpose computer to provide the computer with basic functions, in addition to installing an application to provide functions according to the embodiment. In this case, the program provided according to the embodiment may call on necessary modules from among the program modules provided as a part of the OS in a predetermined sequence at predetermined times in order to carry out relevant processes. In other words, while the program itself according to the embodiment does not contain the above-mentioned modules, the program can carry out processing in collaboration with the OS. The program according to the embodiment may exclude those modules that are provided as a part of the OS.

Moreover, the program according to the embodiment may be combined with and provided as one part of another program. In that case, although as above described the program itself does not include the modules contained in the other program with which it is combined, the program may collaborate with other programs to carry out processing. In other words, the program according to the embodiment may be combined with and provided as one part of another program. Note that the functions provided by executing the program may be implemented in whole or in part as a dedicated hardware circuit.

Figure 4:
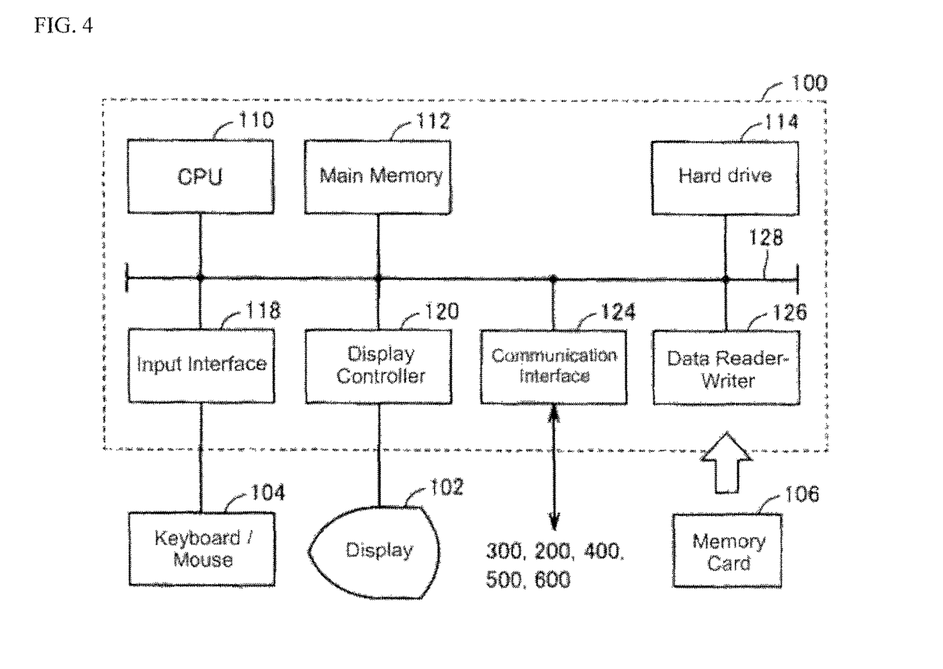
FIG. 4 illustrates a general configuration of a PLC 100 in the first embodiment.

FIG. 4 illustrates a general configuration of a PLC 100 in the first embodiment. Referring to FIG. 4, the PLC 100 includes a central processing unit (CPU) 110 which is an arithmetic processing unit; a main memory 112 and a hard drive 114 as storage units; an input interface 118; a display controller 120; a communication interface 124; and a data reader-writer 126. Each of these components is capable of data communication with each other via a bus 128.

The CPU 110 reads the program (code) installed on the hard drive 114 into main memory 112 and executes the code in a predetermined sequence to thereby carry out various computations. The main memory 112 may be a volatile storage device such as a dynamic random access memory (DRAM) which, in addition to the programs read in from the hard drive 114, stores the input image acquired by the imaging device 250, calibration data for the robot 400, information related to the measurement results, and the like. Moreover the hard drive 114 may store each kind of setting value. Finally, a semiconductor storage device such as flash memory may be used in addition to or as a substitute for the hard drive 114.

The input interface 118 mediates data transmission between the CPU 110 and an input device 104 such as a mouse, a keyboard, a touchscreen panel, and the like. In other words, the input interface 118 receives operation instructions provided by a user operating the input device.

The display controller 120 is connected to a display 102 which is one example of a display device, and controls the display to notify the user of the processing result from the CPU 110. That is, The display controller 120 is connected to a display 102, and controls what is shown on the display 102.

The network interface 124 mediates data transmission between the CPU 110 and other devices in the inspection system such as the inspection units 200, 300, the robot 400 (and more specifically the robot controller 401), the machining device 500, and the post production device 600. The communication interface 124 may be configured by, for example, Ethernet (Registered Trademark), or a universal serial bus (USB).

The data reader-writer 126 mediates the data transmission between the CPU 110 and the memory card 106 which is a recording medium. In other words, the program to be executed on the PLC 100 may be distributed while stored on the memory card 106, and the data reader-writer 126 may read the program out from the memory card 106. The memory card 106 may be a general-purpose semiconductor storage device such as a Compact Flash (CF) card, and a Secure Digital (SD) card; a magnetic storage medium such as a flexible disk; or an optical storage medium such as compact disk read-only memory (CD-ROM).

Other output devices such as a printer may be connected to the PLC 100 as needed.

The Inspection Unit 200

Figure 5:
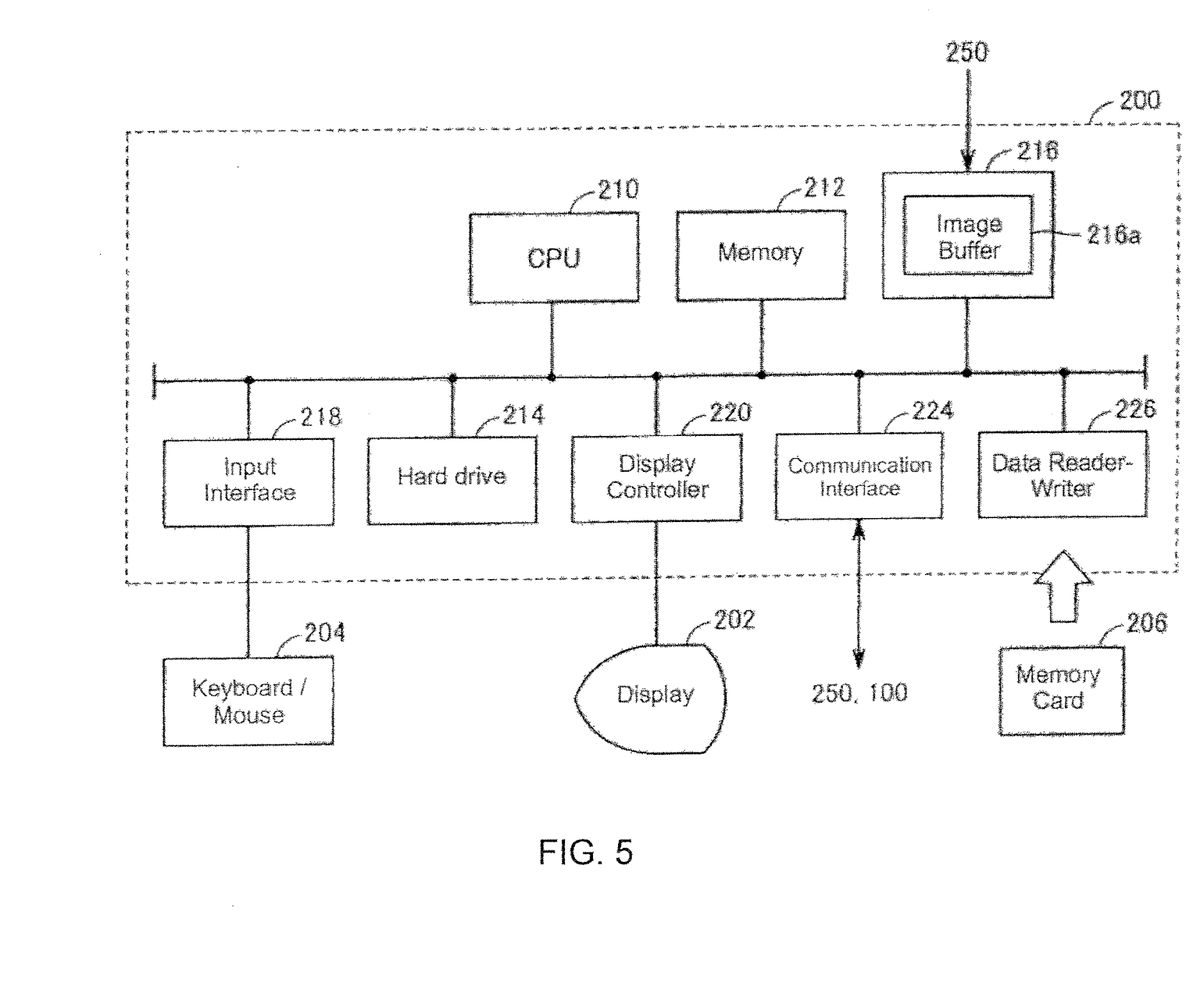
FIG. 5 illustrates a general configuration of the inspection unit 200 according to the first embodiment for processing the image.

FIG. 5 illustrates a general configuration of the inspection unit 200 according to the first embodiment for processing the image. Referring to FIG. 5, the inspection unit 200 includes a central processing unit (CPU) 210; a main memory 212; a hard drive 214; an input interface 218; a display controller 220; a communication interface 224; a camera interface 216; and a data reader-writer 226. Each of these components are capable of data communication with each other via a bus.

The CPU 210 reads the program (code) installed on the hard drive 214 into main memory 212 and executes the code in a predetermined sequence to thereby carry out various computations including processing an image. The main memory 212 may be a volatile storage device such as a dynamic random access memory (DRAM) which, in addition to the programs read in from the hard drive 214, stores the input image acquired by the imaging device 250, and the like.

The input interface 218 mediates data transmission between the CPU 210 and an input device 204 such as a mouse, a keyboard, a touchscreen panel, and the like. The display controller 220 is connected to a display 202, which is one example of a display device, and controls the display to notify the user of the processing result from the CPU 210. The communication interface 224 provides for communication between the CPU 210, and the PLC 100 and imaging device 250.

The data reader-writer 226 mediates the data transmission between the CPU 210 and the memory card 206 which is a recording medium. The memory card 206 is identical to the memory card 106 depicted in FIG. 4.

The camera interface 216 mediates the data transmission between the CPU 210 and the imaging device 250. That is, the camera interface 216 is connected to the imaging device 250 which captures an image of the work piece W and generates an input image. More specifically, the camera interface 216 contains an image buffer 216*a* for temporarily storing an input image from the imaging device 250. Once the input images for a predetermined number of frames are accumulated in the image buffer 216*a*, the camera interface 216 transfers the input images to the main memory 212. The camera interface 216 also provides the imaging device 250 (and more specifically the imaging units 255) with a capture command in accordance with an internal command generated by the CPU 110.

Image Processing Unit

The CPU 210 includes the functions of an image processing unit. The image processing unit carries out processing on an image through the execution of a program. The image data in the image buffer 216*a* includes the identifier of the imaging unit 255 that captured the image. When the location of the imaging units 255 is fixed, having an identifier makes it possible to simultaneously identify the site on the work piece W that was captured because the work piece W is captured in the above described predetermined position. Model image data for each of the sites on a passing workpiece W is stored in the hard drive 214. The image processing unit compares patterns between an image captured by each of the imaging units 255 and a corresponding model image and detects pits or scratches on the surface on the basis of the results of the comparison. The results of the image processing is presented on the display 202.

The Inspection Unit 300

Figure 6:
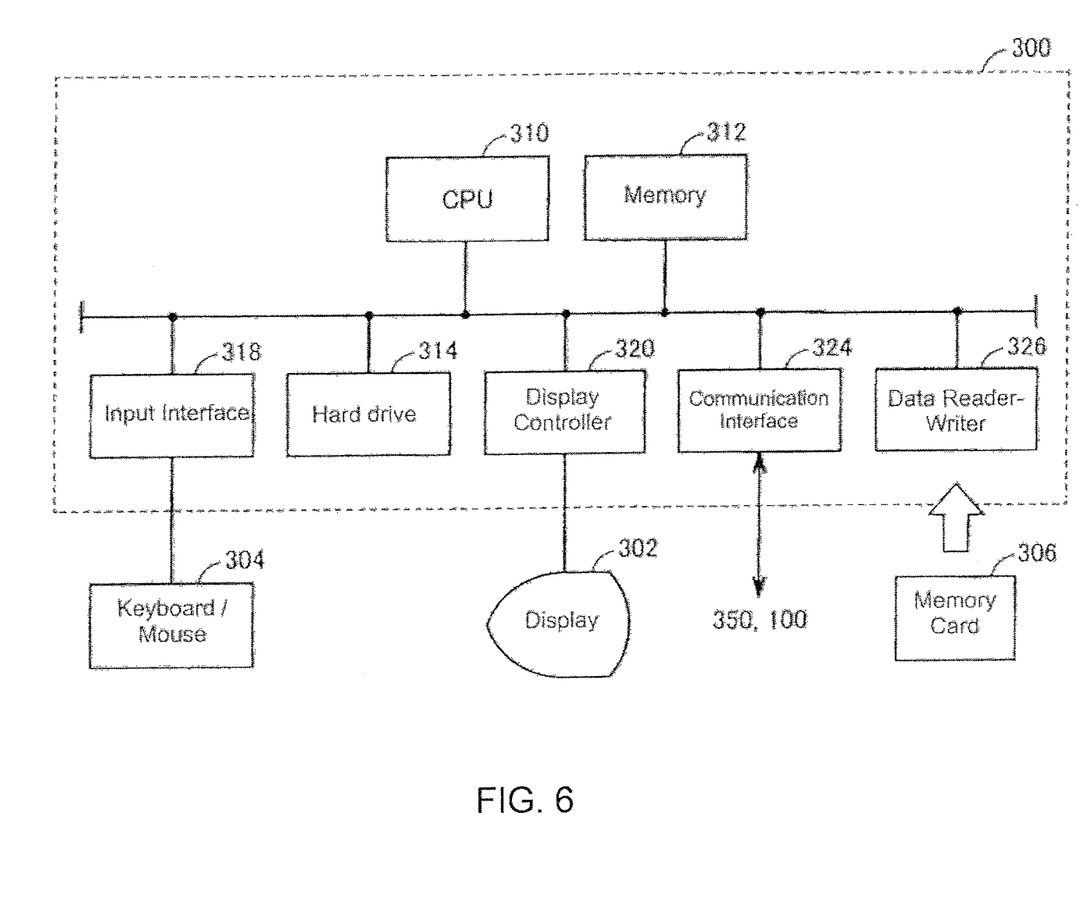
FIG. 6 illustrates a general configuration of an inspection unit 300 according to the first embodiment for processing the measurement data.

FIG. 6 illustrates a general configuration of an inspection unit 300 according to the first embodiment for processing the measurement data. Referring to FIG. 6, the inspection unit 300 includes a central processing unit (CPU) 310; a main memory 312; a hard drive 314; an input interface 318; a display controller 320; a communication interface 324; and a data reader-writer 326. Each of these components is capable of data communication with each other via a bus.

The CPU 310 reads the program (code) installed on the hard drive 314 into main memory 312 and executes the code in a predetermined sequence to thereby carry out various computations including processing an image. The main memory 312 may be a volatile storage device such as a dynamic random access memory (DRAM) which, in addition to the programs read in from the hard drive 314, stores the measurement data acquired by the measurement device 350, and the like.

The input interface 318 mediates data transmission between the CPU 310 and an input device 304 such as a mouse, a keyboard, a touchscreen panel, and the like. The display controller 320 is connected to a display 302 which is one example of a display device, and controls the display to notify the user of the processing result from the CPU 310. The communication interface 324 provides for communication between the CPU 310, and the PLC 100 and measurement device 350.

The data reader-writer 326 mediates the data transmission between the CPU 310 and the memory card 306 which is a recording medium. The memory card 306 is identical to the memory card 106 depicted in FIG. 4.

The camera interface 324 mediates the data transmission between the CPU 310 and the measurement device 350. That is, the communication interface 324 is connected to the measurement device 350 which measures the work piece W and generates measurement data. More specifically, the CPU 310 receives measurement data for the above mentioned sites: the inner diameter (4) and the outer diameter (5), the step (3) and the gap (2) from the measurement device 350 via the communication interface 324. The CPU also provides measurement commands to the measurement device 350 (and more specifically the measurement sensors 353) via the communication interface 324.

Measurement Processing Unit

The CPU 310 includes the functions of a measurement processing unit. The measurement processing unit carries out processing on measurements through the execution of a program. The hard drive 314 stored reference data indicating the outward size of a passing work piece W for use in the measurement processing. The measurement processing unit compares the measurement data received for the inner diameter (4) and the outer diameter (5), the step (3) and the gap (2) and compares the same with the reference data; based on the results of the comparison, the measurement processing unit determines the machining precision such as dimensions and size needed by the machining device 500. The results of the measurement processing is presented on the display 302.

Feedback to Previous Stages

The inspection unit 200 sends the PLC 100 the results of image processing. The inspection unit 300 sends the PLC 100 the results of measurement processing. The PLC 100 determines the parameters needed for the machining device 500 on the basis of the results of image processing and measurement processing; the PLC 100 outputs the parameters determined in the previous stage to the machining device 500. The parameters include parameters that control the operation of the machining device 500. Hereby, the machining device 500 may perform machining in accordance with parameters, whereby it is possible to improve on the work piece W by reducing surface scratches or improving the accuracy of the dimensions and size.

Feedback to Subsequent Stages

The PLC 100 may also evaluate machining precision such as surface machining dimensions and size on the basis of results from imaging processing and measurement processing; the PLC 100 may also send the results of the evaluation to a post production device 600 via the communication interface 224. The post production device 600 determines a grade (categorizes by class) the work pieces W on the basis of the results received from the PLC 100. The grade of a work piece W may be managed in association with an ID read from the work piece W by the code reader 620.

Process Flowchart

Figure 7:
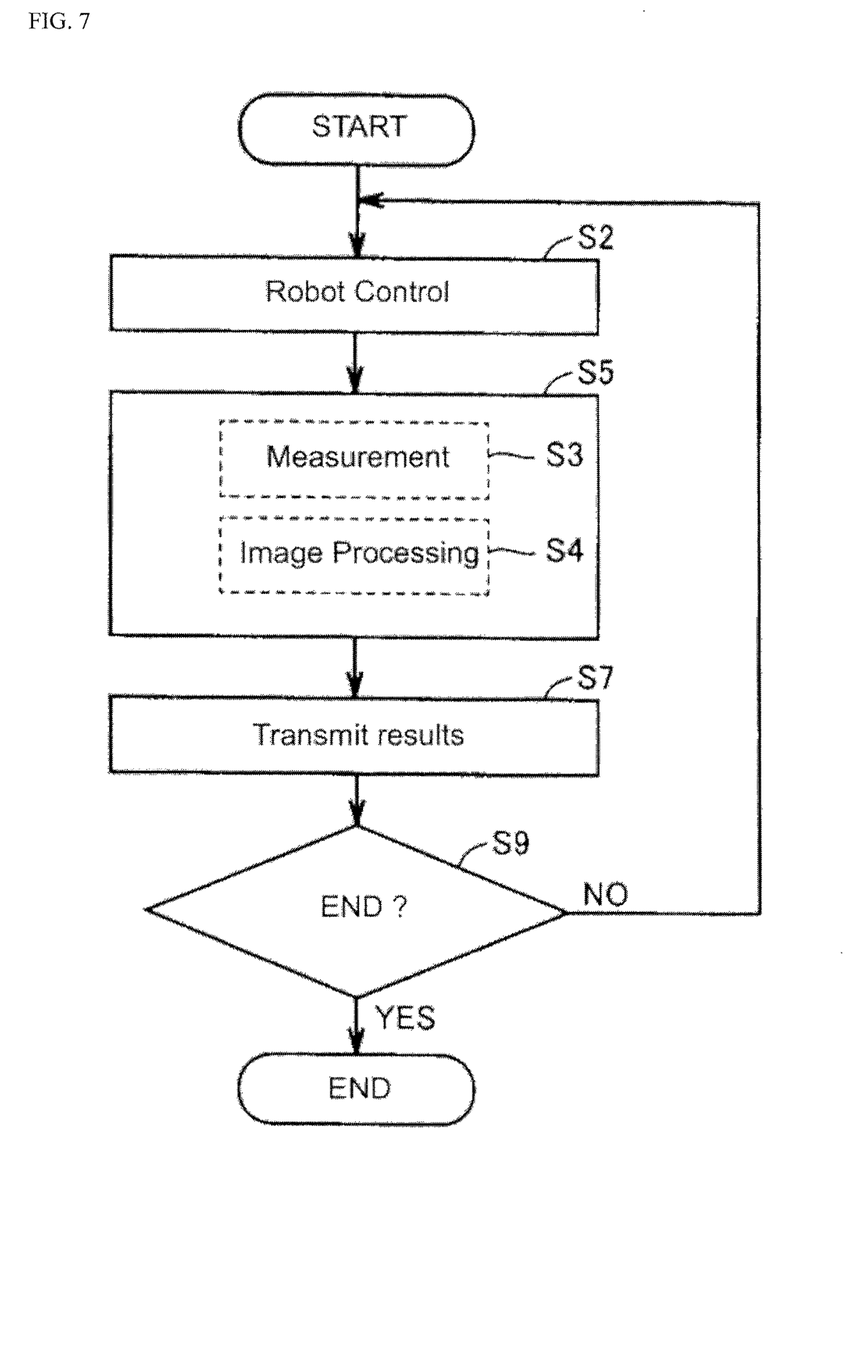
FIG. 7 is a flowchart of an automatic inspection process according to the first embodiment.

FIG. 7 is a flowchart of an automatic inspection process according to the first embodiment. A program following this flowchart may be stored in advance on a storage unit in the PLC 100, and executed by the CPU 110.

First, the PLC 100 sends a control signal to the robot 400. Hereby, the first support 410 of the robot 400 grabs the work piece W so that the work piece W is in a predetermined position (step S2). The first support 410 moves along the direction of the axis AR (FIG. 2) to thereby move the work piece W linearly along the direction of the axis AR while the work piece W is in the predetermined position.

The work piece W passes through the second through hole 360 of the measurement device 350 and then passes through the first through hole 260 of the imaging device 250 when moving along the direction of the axis AR. The inspection process is carried out when the work piece W passes through the through holes (step S5).

The above-described measurement process (step S3), and the imaging process (step S4) are carried out when the work piece W passes through the second through hole 360 and passes through the first through hole 260 respectively during the inspection process (step S5).

The PLC 100 provides feedback to the above-mentioned previous stage and feedforward to the above-mentioned subsequent stage on the basis of the results of the imaging process and the measurement process (step S7).

It is then determined whether or not all the work pieces have been inspected (step S9). For instance, the CPU 110 in the PLC 100 may determine whether or not to terminate the inspection process on the basis of a user command entered from the input device 104. If it is determined that processing is not to be terminated (No, at step S9), the processing returns to step S2 and executes the inspection process after step S2 in the same manner. If it is determined that processing is to be terminated (Yes, at step S9) the series of processes ends.

Example of a Modified Barrel

Figure 8:
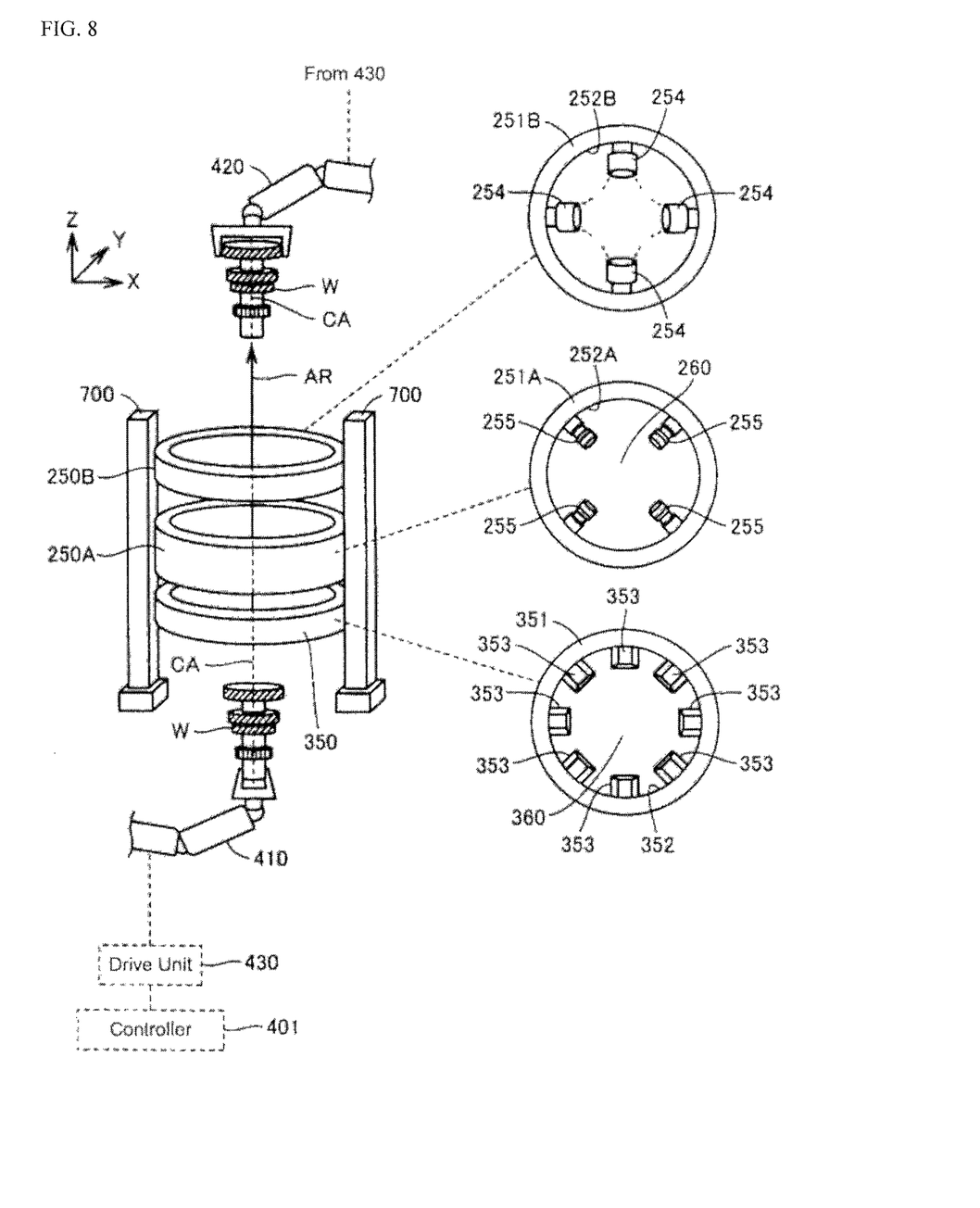
FIG. 8 illustrates an example of modifying a first barrel according to the first embodiment.

FIG. 8 illustrates an example of modifying the first barrel according to the first embodiment. In FIG. 2 the illumination device 254 is provided to the first barrel 251 together with the imaging units 255; however, the illumination device 254 is not limited to being disposed on the first barrel 251. For example, the inspection system may be provided with an imaging device 250 that is separated into a first device 250A onto which the imaging units 255 may be installed, and a second device 250B onto which the illumination device 254 may be installed (FIG. 8).

The second device 250B includes a substantially column-shaped third barrel 251 stacked on top of the first barrel 251A of the first device 250A. The third barrel 251B includes a third through hole through which a work piece W may pass. In FIG. 8, one or a plurality of illumination devices 254 is disposed on the inner peripheral surface 252B of the third through hole in the third barrel 251B, and the imaging units 255 are disposed on the inner peripheral surface 252A of the first barrel 251A.

The illumination devices 254 in the third barrel 251B may be installed on an angle that illuminates the inside of the first through hole 260 in the first barrel 251A; hereby, allowing illumination light to enter inside the first through hole makes it possible to satisfy certain illumination conditions when capturing an image. Note that although the third barrel 251B is stacked above the first barrel 251A in FIG. 8, the third barrel 251B may be arranged below the first barrel 251A.

Advantages

Figure 9:
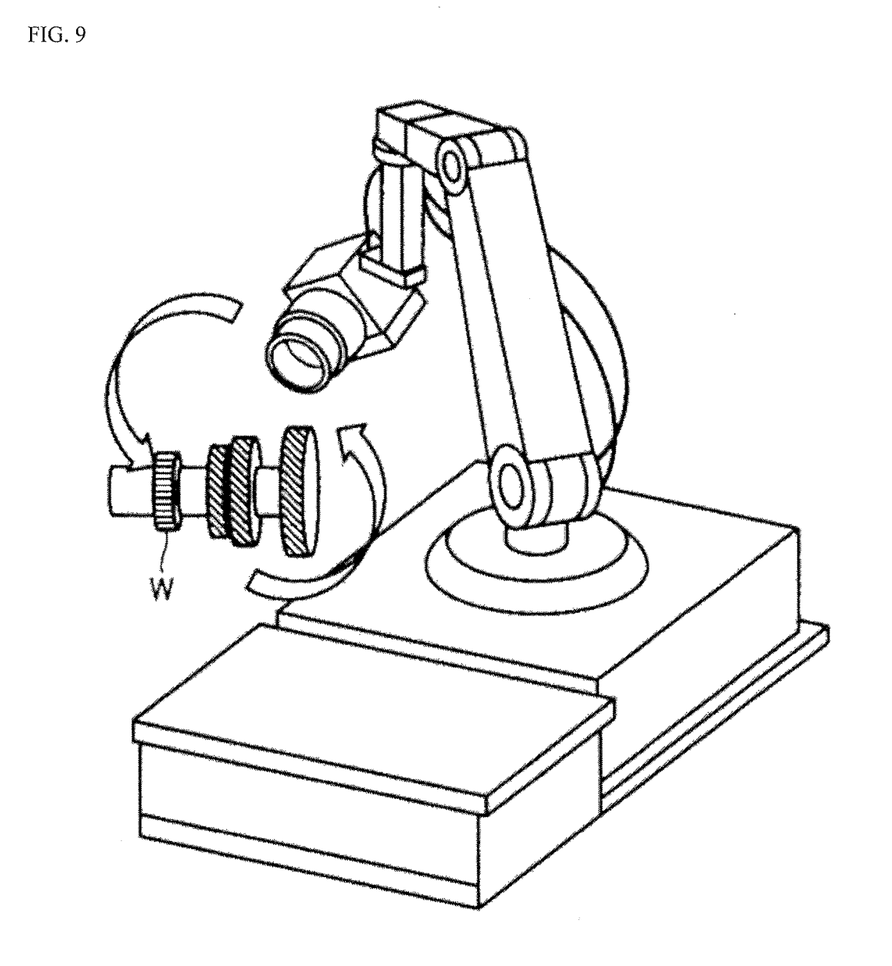
FIG. 9 is a schematic view of another inspection device to illustrate the advantages of the inspection system according to the first embodiment.

FIG. 9 is a schematic view of another inspection device to illustrate the advantages of the inspection system according to the first embodiment. In another inspection device, a camera is installed on the robot arm (FIG. 9). During inspection, the robot arm rotates so that the camera moves about the work piece W, allowing the device to capture the entire work piece, which is stationary. This requires that the timing used by the camera to capture image and the movement of the robot arm are integrated and mutually synchronized; however, this timing may not be within a required turnaround time.

In contrast, the inspection device according to the first embodiment can capture an image of and measure the work piece W from all directions all at once by having the first support 410 of the robot 400 move the work piece W via a through hole along an axis AR. Accordingly, there is no need to synchronize when an image is captured with the rotation of the robot arm. Therefore, this reduces the amount of time required for inspection, and allows the inspection to coincide with the required turnaround time.

Second Embodiment

The second embodiment provides explanation of modifications to the first embodiment.

Measurement from Image Data

The measurement device 350 is provided in the above embodiment to take measurements; however, the measurement device 350 may be excluded when it is possible to obtain measurement data from the image captured. For example, the imaging unit 255 may be a 3-D camera for taking three-dimensional measurements of the work piece W from the image captured. In this case, the 3-D image output from the 3-D camera may be used as the basis for detecting contours or topography of the surface of the work piece W. Any cracks or scratches in the work piece W may be examined by comparing the 3D image data obtained to 3D CAD data, or by creating a two-dimensional image from the 3D image.

Finally, in the above-mentioned embodiment the imaging device 250 and the measurement device 350 are provided in different barrels in the inspection system; however these devices may be provided in the same barrel.

Example of a Modified Illumination Unit

The illumination device provided to the imaging device 250 may be an illumination ring (capable of providing illumination from 360°) provided on the inner peripheral surface of the first through hole 260 along the shape of the opening. In this case, certain problems can be more reliably avoided since shadows tend not to form on the surface of the work piece. More specifically, problems where halation occurs due to the specular reflection of illumination light entering the imaging units 255, or where the work piece W has a mirrored surface whereby the light source itself form an image on the surface of the work piece W.

Excluding the Illumination Device

The illumination devices 254 (FIG. 2) may be eliminated. More specifically, the illumination devices 254 may be excluded when ambient lighting such as the illumination light from a ceiling fixture in a room sufficiently satisfies the imaging criteria, if the imaging device 250 is arranged above and the measurement device 350 is arranged below along the extending direction of the Z axis in FIG. 2.

Modular System Configuration

Referring to FIG. 2, the imaging device 250 and the measurement device 350 may be mounted for attachment to and detachment from stanchions 700 without being permanently fixed thereto. In this case, the imaging device 250 and the measurement device 350 may be removed by shifting the same vertically along the stanchions 700 (i.e., the direction the Z axis extends) or along the length thereof (i.e., the direction the Y axis extends). This facilitates swapping in and out various types of imaging devices 250 or measurement devices 350 in accordance with the type of inspection to be performed or the size of the work piece W.

Integration of the PLC and the Inspection Device

The PLC 100, the inspection unit 200, and the inspection unit 300 are provided individually in the first embodiment; however, these components may be provided as a single unit. In that case, the functions of the inspection units 200 and 300 may be assembled into the PLC 100.

All aspects of the embodiments disclosed should be considered merely examples and not limitations as such. The scope of the present invention is not limited to the above description but to the description in the claims, and is intended to include all equivalents and modifications allowable by the claims.

The invention claimed is:

1. An inspection system comprising: an inspection device configured to examine the external features of an object; and a control device for controlling the inspection device;
   the inspection device comprising:
     a substantially column-shaped first barrel that includes a first through hole configured for an object to pass therethrough; and
     a plurality of cameras provided on the inner peripheral surface which forms the first through hole in the first barrel; and
   the control device comprising:
     an image processing unit configured to process an image captured and output by each of the cameras for the purpose of inspection; and
     a communication unit configured for communication with an external device;
   the external device including:
     a support device including a first support configured to support the object; and
     a drive unit; and
   the control device causing the communication unit to transmit a control signal to the support device, said control signal configured to control the drive unit to cause the first support to pass through the first through hole while supporting the object.

2. The inspection system according to claim 1, wherein the support device further includes a second support configured to support the object; and the control device causing the communication unit to transmit a control signal to the support device, said control signal configured to control the drive unit to cause the second support to receive the object from the first support after the first support passes through the first through hole.

3. The inspection system according to claim 2, wherein the inspection device further includes a light source configured to illuminate inside the first through hole.

4. The inspection system according to claim 3, further comprising: a plurality of measurement sensors provided on the inner peripheral surface of the first barrel and configured to measure the external features of the object;
the control device including:
a measurement processing unit configured to process the measurement values output from the measurement sensors for the purpose of inspection.

5. The inspection system according to claim 3, with the inspection device further comprising: a substantially column-shaped second barrel that includes a second through hole configured for the object to pass therethrough; and a plurality of measurement sensors provided on the inner peripheral surface which forms the second through hole in the second barrel and configured to measure the external features of the object;
the control device including:
a measurement processing unit configured to process the measurement values output from the measurement sensors for the purpose of inspection.

6. The inspection system according to claim 5, wherein the first barrel and the second barrel are stacked along a virtual axis passing through the first through hole and the second through hole, with said virtual axis corresponding to a route along which the object passes.

7. An inspection system comprising: an inspection device configured to examine the external features of an object; and a control device for controlling the inspection device;
the inspection device including:
a substantially column-shaped barrel that includes a through hole configured for an object to pass therethrough;
a light source configured to illuminate inside the through hole; and
a plurality of measurement sensors provided on the inner peripheral surface of the barrel and configured to measure the external features of the object;
the control device including:
a measurement processing unit configured to process the measurement values output from the measurement sensors for the purpose of inspection; and
a communication unit configured for communication with an external device;
the external device including:
a support device including a support configured to support the object; and
a drive unit; and
the control device causing the communication unit to transmit a control signal to the support device, said control signal configured to control the drive unit to cause the support to pass through the through hole while supporting the object.

8. An inspection system comprising: an inspection device configured to examine the external features of an object; and a control device for controlling the inspection device;
the inspection device comprising:
a substantially column-shaped first barrel that includes a first through hole configured for an object to pass therethrough;
a plurality of cameras provided on the inner peripheral surface which forms the first through hole in the first barrel; and
a light source configured to illuminate inside the first through hole; and
the control device comprising:
an image processing unit configured to process an image captured and output by each of the cameras for the purpose of inspection; and
a communication unit configured for communication with an external device;
the external device including:
a support device including a first support configured to support the object; and
a drive unit; and
the control device causing the communication unit to transmit a control signal to the support device, said control signal configured to control the drive unit to cause the first support to pass through the first through hole while supporting the object.

9. An inspection system comprising: an inspection device configured to examine the external features of an object; and a control device for controlling the inspection device;
the inspection device comprising:
a substantially column-shaped first barrel that includes a first through hole configured for an object to pass therethrough; and
a plurality of cameras provided on the inner peripheral surface which forms the first through hole in the first barrel; and
a plurality of measurement sensors provided on the inner peripheral surface of the first barrel and configured to measure the external features of the object; and
the control device comprising:
an image processing unit configured to process an image captured and output by each of the cameras for the purpose of inspection;
a measurement processing unit configured to process the measurement values output from the measurement sensors for the purpose of inspection; and
a communication unit configured for communication with an external device;
the external device including:
a support device including a first support configured to support the object; and
a drive unit; and
the control device causing the communication unit to transmit a control signal to the support device, said control signal configured to control the drive unit to cause the first support to pass through the first through hole while supporting the object.

10. The inspection system according to claim 9, wherein the support device further includes a second support configured to support the object; and
the control device causing the communication unit to transmit a control signal to the support device, said control signal configured to control the drive unit to cause the second support to receive the object from the first support after the first support passes through the first through hole.

11. An inspection system comprising: an inspection device configured to examine the external features of an object; and a control device for controlling the inspection device;

the inspection device comprising:
   a substantially column-shaped first barrel that includes a first through hole configured for an object to pass therethrough;
   a plurality of cameras provided on the inner peripheral surface which forms the first through hole in the first barrel;
   a substantially column-shaped second barrel that includes a second through hole configured for the object to pass therethrough; and
   a plurality of measurement sensors provided on the inner peripheral surface which forms the second through hole in the second barrel and configured to measure the external features of the object;

the control device comprising:
   a measurement processing unit configured to process the measurement values output from the measurement sensors for the purpose of inspection; and
   an image processing unit configured to process an image captured and output by each of the cameras for the purpose of inspection.

12. The inspection system according to claim 11, with the control device further comprising: a communication unit configured for communication with an external device;
   the external device including:
      a support device including a first support configured to support the object; and
      a drive unit; and
   the control device causing the communication unit to transmit a control signal to the support device, said control signal configured to control the drive unit to cause the first support to pass through the first through hole while supporting the object.

13. The inspection system according to claim 12, wherein the support device further includes a second support configured to support the object; and
   the control device causing the communication unit to transmit a control signal to the support device, said control signal configured to control the drive unit to cause the second support to receive the object from the first support after the first support passes through the first through hole.

14. The inspection system according to claim 11, wherein the first barrel and the second barrel are stacked along a virtual axis passing through the first through hole and the second through hole, with said virtual axis corresponding to a route along which the object passes.

15. The inspection system according to claim 14, with the control device further comprising: a communication unit configured for communication with an external device;
   the external device including:
      a support device including a first support configured to support the object; and
      a drive unit; and
   the control device causing the communication unit to transmit a control signal to the support device, said control signal configured to control the drive unit to cause the first support to pass through the first through hole while supporting the object.

16. The inspection system according to claim 15, wherein the support device further includes a second support configured to support the object; and
   the control device causing the communication unit to transmit a control signal to the support device, said control signal configured to control the drive unit to cause the second support to receive the object from the first support after the first support passes through the first through hole.

\* \* \* \* \*